US007671224B2

(12) United States Patent
Winde et al.

(10) Patent No.: US 7,671,224 B2
(45) Date of Patent: Mar. 2, 2010

(54) USE OF A PHOSPHORUS CONTAINING LIGAND AND A CYCLIC ORGANIC LIGAND IN A TRANSITION METAL COMPOUND

(75) Inventors: Roland Winde, Frankfurt (DE); Ralf Wilhelm Karch, Kleinostheim (DE); Andreas Rivas-Nass, Kelkheim (DE); Oliver Briel, Offenbach/Main (DE); Robert Paul Tooze, St. Andrews Fife (GB); Grant Stephen Forman, St. Andrews Fife (GB); Wolfgang Hubert Meyer, Johannesburg (ZA)

(73) Assignee: Umicore AG & Co. KG, Hanau-Wolfgang (DE)

( * ) Notice: Subject to any disclaimer, the term of this patent is extended or adjusted under 35 U.S.C. 154(b) by 0 days.

(21) Appl. No.: 11/995,442

(22) PCT Filed: Jul. 12, 2006

(86) PCT No.: PCT/IB2006/052374

§ 371 (c)(1),
(2), (4) Date: May 12, 2008

(87) PCT Pub. No.: WO2007/010453

PCT Pub. Date: Jan. 25, 2007

(65) Prior Publication Data

US 2008/0221345 A1     Sep. 11, 2008

(30) Foreign Application Priority Data

Jul. 15, 2005   (GB) ................................. 0514612.1

(51) Int. Cl.
*C07F 15/00*   (2006.01)
*B01J 31/00*   (2006.01)

(52) U.S. Cl. .................. 556/21; 556/136; 548/103; 502/155

(58) Field of Classification Search .............. 556/21, 556/136; 548/103; 502/155
See application file for complete search history.

(56) References Cited

FOREIGN PATENT DOCUMENTS

WO    WO 2004/005223 A1   1/2004
WO    WO 2007/010453 A3   1/2007

OTHER PUBLICATIONS

Chen A C et al., "Synthesis, structure determination, and hydroformylation activity of N-heterocylclic carbene complexes of rhodium," Can J Chem, vol. 83, 943-57 (Jun. 2005).
Hardman N J et al "Molecular and electronic stgructure of platinum Bis (N-arylamino) phosphenium complexes including [Pt(phosphane)(phosphenium)-(N-heterocyclic carbene)]," Angewandte Chemie, International Edition, vol. 43, No. 15, Apr. 2, 2004 pp. 1955-1958.
Furstner A: "Olefin metathesis and beyond," Angewandte Chemie, International Edition, vol. 39, 2000 pp. 3012-3043.
Jarfarpour L et al. "Indenylidene-imidazolylidene complexes of ruthenium as ring-closing metathesis catalysts" Orgnometallics, vol. 18,No. 25, Nov. 10, 1999, pp. 5416-5419.
Furstner A et al., "Indenylidene Complexes of Ruthenium: Optimized Synthesis, Structure Elucidation, and Perfomance as Catalysts for Olefin Metathesis—Application to the Synthesis of the ADE-ring system of Nakadomomarin A" Chemistry, A European Journal, vol. 7, No. 22, 2001, pp. 4811-4820.
Opstal T et al., "From atom transfer radical addition to atom transfer radical polymerisation of vinyl monomers mediated by ruthenium indenylidene complexes," New Journal of Chemistry, vol. 27 No. 2, Feb. 1, 2003, pp. 257-262.
Opstal T et al., "Ruthenium indenylidene and vinylidene complexes bearing Schiff bases: potential catalysts in enol-ester synthesis," Synlett, no. 6, 2002, pp. 935-941.
Randl S et al., "Highly Selective cross metathesis with acrylnitrile using a phospine free Ru-complex," Synlett, No. 3, 2001, pp. 430-432.
Trnka T M et al., "The development of L2X2Ru=CHR olefin metathesis catalysts: an organometallic success story," Accounts Chem. Res. 34:1 2001, pp. 18-29.
Scholl M et al., "Increased ring closing metathesis activity of ruthenium-based olefin metathesis catalysts coordinated with imidazolin-2-ylidne ligands" Tetrahedron Letters, vol. 40 No. 12, Mar. 19, 1999, pp. 2247-2250.
Weskamp T et al., "A Novel Class of Ruthenium Catalysts for Olefin metathesis," Angewandte Chemie, International Edition, 37:18, 1998 pp. 2490-2493.
Dias E L et al., "Well-defined ruthenium olefin metathesis catalysts: Mechanism and activity," Journal of the American Chemical Society, vol. 119, No. 17, 1997, pp. 3887-3897.
Harlow K J et al., "The first co-ordinatively unsaturated Group 8 allenylidene complexes: insights into Grubbs' vs.Dixneuf-Furstner olefin metathesis catalysts" Journal of the Chemical Society, Dalton Transactions, 1999, pp. 285-291.
Furstner A et al., "Coordinatively unsaturated ruthenium allenylidene complexes: Highly effective, well defined catalysts for the ring-closure metathesis of alpha, omega-dienes and dienynes," Chemical Communications, 5:7, Apr. 7, 1999, pp. 601-602.

(Continued)

*Primary Examiner*—Porfirio Nazario Gonzalez
(74) *Attorney, Agent, or Firm*—Kalow & Springut LLP; John J. Santalone

(57) ABSTRACT

According to the present invention there is provided a compound in the form of a transition metal compound including a transition metal, a phosphorus containing ligand, and a cyclic organic ligand. The phosphorus containing ligand is a heterocyclic organic compound with a ligating phosphorus atom which ligates with the transition metal, and which ligating phosphorus atom is an atom in the heterocyclic ring structure of the heterocyclic organic compound. The cyclic organic ligand is a cyclic organic compound with a ligating carbon atom in the cyclic ring structure of the cyclic organic compound which ligates with the transition metal by means of a double bound. The invention also relates to a method preparing such a compound and a metathesis reaction wherein such a compound is used as a catalyst.

35 Claims, 1 Drawing Sheet

OTHER PUBLICATIONS

Forman, et al., J. Organometallic Chemistry, vol. 691, pp. 5513-5516 (2006).

H-J Schanz, L Jafarpour, S Nolan, Organometallics, 1999, 18, 5187-5190.

Boeda, et al., J. Org. Chem., vol. 73, pp. 259-263 (2008).

USE OF A PHOSPHORUS CONTAINING LIGAND AND A CYCLIC ORGANIC LIGAND IN A TRANSITION METAL COMPOUND

TECHNICAL FIELD

The invention relates to the use of a phosphorus containing ligand and a cyclic organic ligand in a transition metal compound and to the use of a phosphorus containing ligand and cyclic organic ligand in a catalysed reaction, preferably a metathesis reaction. The invention also relates to a compound including such a phosphorus containing ligand and cyclic organic ligand; and to a metathesis reaction using the said catalyst. The invention further relates to a method of preparing such a catalyst.

BACKGROUND TO THE INVENTION

There is considerable interest regarding the formation of carbon-carbon bonds via olefin metathesis. Olefin metathesis refers to the metal-catalysed redistribution of carbon-carbon double bonds. Cross metathesis (CM) can be described as a metathesis reaction between two non-cyclic olefins, which may be the same or different, for example:

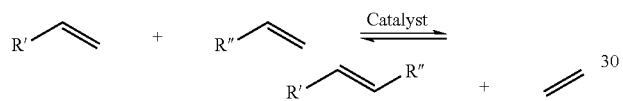

Where the olefins are the same, the reaction is known as self metathesis.

Ring-opening metathesis polymerization (ROMP) is a variant of olefin metathesis reactions wherein cyclic olefins (for example) produce polymers and co-polymers, for example:

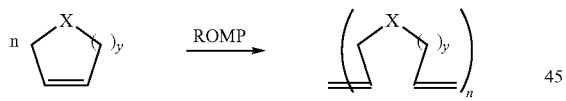

Ring-closing metathesis (RCM) represents a process in which an acyclic diene (for example) is cyclised to produce a cycloalkene, for example;

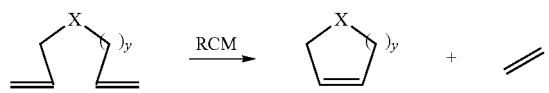

As indicated above metathesis reactions take place in the presence of a catalyst. A great deal of research has been done in an attempt to synthesise and isolate catalysts which are able to catalyse homogeneous olefin metathesis reactions. More particularly the synthesis of Group VIII transition metal metathesis catalysts has led to catalysts with increased functional group tolerance and stability with respect to conditions such as air, water and acids.

During the 1990's the so-called "1st generation Grubbs catalyst" of formula 1a was developed:

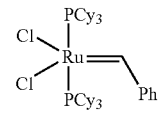

where Cy is cyclohexyl.

This well defined ruthenium catalyst afforded high selectivities, high reaction rates and good tolerance for oxygenates in feed during homogeneous olefin metathesis reactions, including cross metathesis, ring closing metathesis and ring opening metathesis polymerisation. These processes have many potential commercial applications for the commodities, pharmaceutical and fine chemicals industries as well as in the field of speciality polymers. Several reviews describe the development and applications of Grubbs-type catalysts (for example Acc. Chem. Res. 2001, 34, 18-24; Angew. Chem., Int. Ed., 2000, 39, 3012-3043).

Much research has been carried out to investigate the effect of changing the nature of the ligands, (for example J. Am. Chem. Soc. 1997, 119, 3887-3897; Tetrahedron Lett. 1999, 40, 2247-2250; Angew. Chem., Int. Ed. 1998, 37, 2490-2493) resulting in the development of second generation Grubbs catalysts. The main thrust of second generation Grubbs catalyst research has related to a move away from the use of phosphine ligands to the use of highly nucleophilic N-heterocyclic carbenes for homogeneous metathesis reactions. Formula 1b shows the structure of the standard second generation Grubbs catalyst. While this catalyst shows greater reactivity compared to catalyst 1a, it is more expensive than the first generation catalyst.

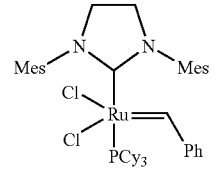

where Cy=cyclohexyl, and Mes=mesityl

WO ZA03/00087 discloses the use of a phosphorus containing ligand as a ligand for a metathesis catalyst in a catalysed metathesis reaction wherein the phosphorus containing ligand is a heterocyclic organic compound with a ligating phosphorus atom as an atom in the heterocyclic ring structure of the heterocyclic organic compound.

A major disadvantage of complexes depicted by formula 1a relates to their preparation which requires either reagents which are hazardous (e.g. potentially explosive diazoalkanes), or difficult to prepare (e.g. diphenylcyclopropene), or extremely sensitive.

As a result there exists a need to develop efficient routes to these complexes where
1. The individual components (ligands and alkylidene) are inexpensive, non-hazardous and scaleable
2. The reaction to prepare the Ru-alkylidene-type olefin metathesis catalyst that uses the individual components as reagents is straight-forward, non-hazardous and can be performed on the multi-kilogram scale economically.

It has now been found that relatively inexpensive phosphorus containing ligands such as phosphabicylononane ligands, when combined with a specific alkylidene-type moiety such as the indenylidene alkylidene moiety provide a non-hazardous, economical Ru-alkylidene-type olefin metathesis catalysts. These catalysts or catalyst precursors are usually easy to prepare from well accessible, stable and essentially non-toxic starting materials and can usually be isolated and stored. At least some of these catalysts exhibit high catalytic activity, a good compatibility with functional groups, solvents, water and additives, and they need not to be activated by any additive.

An indenylidene ruthenium complex was first synthesized by Hill (*J. Chem. Soc.*, Dalton Trans. 1999, 285), who incorrectly assigned the structure of the diphenylallenylidene complex. Together with Fürstner the complex was used in various ring-closing metathesis reactions (Chem. Commun. 1999, 601-602). Later detailed evaluations showed that the correct structure is the rearranged indenylidene complex (*Organometallics* 1999, 18, 5416-5419, *Chem. Eur. J.* 2001, 7, 4811-4820). Still, this complex was only used in RCM by Fürstner in the synthesis of natural products.

In 2003 F. Verpoort published the use of this complex in the Atom Transfer Radical Addition (ATRA), *New J. Chem.* 2003, 27, 257-262. Several different olefins have been used in the ATRA with carbon tetrachloride in good to nearly quantitative yields. Verpoort also used the complex in the nucleophilic addition of carboxylic acids to terminal alkynes (*Synlett* 2002, 935-941), e.g. formic acid, acetic acid, isovaleric acid, or benzoic acid to t-Butylacetylene, 1,7-octadiyne or 4-pentynoic acid. Here the catalyst showed moderate yields. Blechert (*Synlett* 2001, 3, 430-432) used the catalyst as a precursor for other metathesis catalysts.

The indenylidene complexes as described above did not include a phosphorus containing ligand which is a heterocyclic organic compound with a ligating phosphorous atom as an atom in the heterocyclic ring structure of the heterocyclic organic compound.

SUMMARY OF THE INVENTION

According to the present invention there is provided a compound in the form of a transition metal compound including a transition metal, a phosphorus containing ligand, and a cyclic organic ligand. The phosphorus containing ligand is a heterocyclic organic compound with a ligating phosphorus atom which ligates with the transition metal, and which ligating phosphorus atom is an atom in the heterocyclic ring structure of the heterocyclic organic compound. The cyclic organic ligand is a cyclic organic compound with a ligating carbon atom in the cyclic ring structure of the cyclic organic compound which ligates with the transition metal by means of a double bound. The invention also relates to a method preparing such a compound and a metathesis reaction wherein such a compound is used as a catalyst.

DETAILED DESCRIPTION OF THE INVENTION

Figure 1:
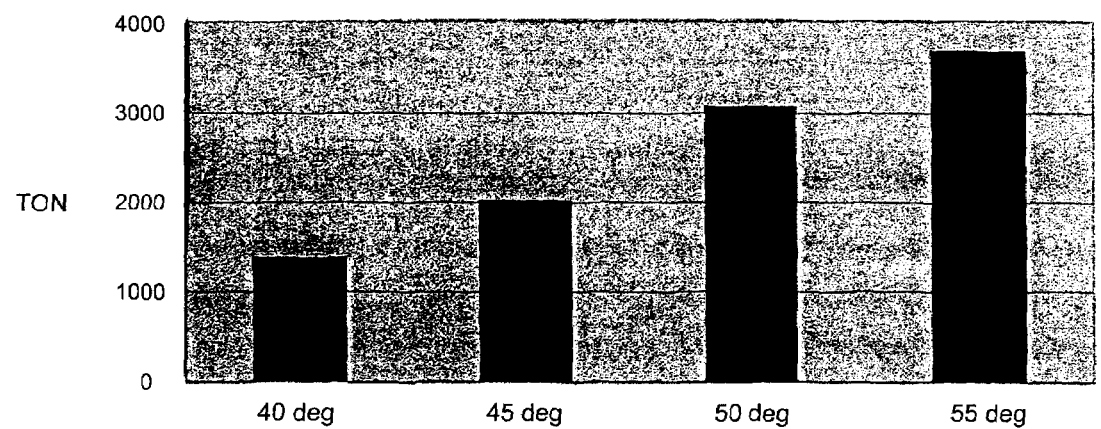
FIG. 1: shows the productive turnover obtained using catalyst (12) (S/C=10 000:1) at 10 bar ethylene pressure at various temperatures

According to a first aspect of the present invention there is provided the use of a phosphorus containing ligand and a cyclic organic ligand as ligands for a catalyst in the form of a transition metal compound containing a transition metal; wherein the phosphorus containing ligand is a heterocyclic organic compound with a ligating phosphorus atom which ligates with the transition metal, and which ligating phosphorus atom is an atom in the heterocyclic ring structure of the heterocyclic organic compound; and wherein the cyclic organic ligand is a cyclic organic compound with a ligating carbon atom in the cyclic ring structure of the cyclic organic compound which ligates with the transition metal by means of a double bond.

Preferably the catalyst is a metathesis catalyst.

According to a second aspect of the present invention there is provided the use of a phosphorus containing ligand and a cyclic organic ligand in the preparation of a transition metal compound catalyst including a transition metal, the phosphorus containing ligand and the cyclic organic ligand; wherein the phosphorus containing ligand is a heterocyclic organic compound with a ligating phosphorus atom which ligates with the transition metal, and which ligating phosphorus atom is an atom in the heterocyclic ring structure of the heterocyclic organic compound; and wherein the cyclic organic ligand is a cyclic organic compound with a ligating carbon atom in the cyclic ring structure of the cyclic organic compound which ligates with the transition metal by means of a double bond.

Preferably the catalyst is for use in a metathesis reaction.

According to a third aspect of the present invention there is provided a compound in the form of a transition metal compound including a transition metal, a phosphorus containing ligand, and a cyclic organic ligand; wherein the phosphorus containing ligand is a heterocyclic organic compound with a ligating phosphorus atom which ligates with the transition metal, and which ligating phosphorus atom is an atom in the heterocyclic ring structure of the heterocyclic organic compound; and wherein the cyclic organic ligand is a cyclic organic compound with a ligating carbon atom in the cyclic ring structure of the cyclic organic compound which ligates with the transition metal by means of a double bound.

Preferably the compound is a catalyst, and preferably the catalyst is a metathesis catalyst.

Preferably the metathesis reaction/catalyst is a homogenous metathesis reaction/catalyst, or a reaction with an immobilized preformed catalyst.

Preferably the ligating phosphorus atom is also bound to a further moiety which is not part of the heterocyclic ring structure.

Preferably the phosphorus containing ligand comprises a phosphine ligand, preferably a secondary or tertiary phosphine ligand, preferably a tertiary phosphine ligand. The further moiety bound to the ligating phosphorus atom may be an atom, and preferably it is H. In an alternative and preferred embodiment of the invention the said moiety may comprise an organic group, preferably an organyl group. The organyl group may comprise an alkyl, alkenyl, alkynyl, aryl, cycloalkyl, cycloalkenyl, cycloalkynyl and optionally it may be substituted. Preferably it comprises an alkyl, cycloalkyl or aryl.

Preferably the heterocyclic organic compound has a single heteroatom in the form of the ligating phosphorus atom.

The heterocyclic organic compound may comprise a bicyclic organic compound. Preferably the heterocyclic organic compound includes no unsaturated carbon to carbon bonds. Preferably the two ring structures have at least 3 shared atoms. Preferably the two ring structures do not have more than 12 ring atoms, preferably they have nine ring atoms.

In a preferred embodiment of the invention the phosphine ligand comprises a bicyclic tertiary phosphine having a ligating phosphorus atom which is preferably bound to two first atoms (preferably carbon atoms) in the ring structure with each of said first atoms being bound to two other second atoms (preferably carbon atoms) in the ring structure. Preferably both the second atoms are carbon atoms. It will be appreciated that in this embodiment each first atom is bound to three ring atoms.

In a preferred embodiment of the invention the heterocyclic organic compound comprises a phosphacycloalkane, preferably a phosphabicycloalkane, preferably a phosphabicyclononane, each of which optionally may be substituted. Preferably it comprises a monophosphacycloalkane, preferably a monophosphabicycloalkane, preferably a monophosphabicyclononane. Preferably the compound comprises a tertiary phosphine.

In a preferred embodiment of the invention, the phosphabicyclononane is a 9-phosphabicyclo[3.3.1]nonane of formula 2a or a 9-phosphabicyclo[4.2.1]nonane of formula 2b or mixtures thereof:

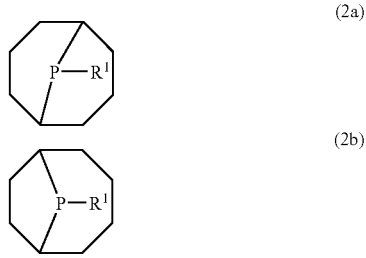

wherein $R^1$ is H or an organic group (including an organyl group). Preferably $R^1$ is an optionally substituted alkyl, or optionally substituted aryl, or an optionally substituted cycloalkyl.

The phosphabicyclononane may be a compound of formula 2a.

In one embodiment of the invention $R^1$ is alkyl, preferably —$C_{20}H_{41}$ also known as eicosyl. In this instance the ligand is known as eicosyl phoban (that is for both compounds of formula 2a and 2b where $R^1$ is —$C_{20}H_{41}$).

In one preferred embodiment of the invention $R^1$ is cyclohexyl. In this instance the ligand is known as cyclohexyl phoban (that is for both compounds of formula 2a and 2b where $R^1$ is cyclohexyl).

The cyclic ring structure of the cyclic organic ligand may be a heterocyclic ring structure, but preferably it is a homocyclic ring structure.

The ring structure which includes the ligating carbon atom may be saturated, but preferably it is unsaturated. The ring structure including the ligating carbon atom may be monocyclic, but preferably it is polycyclic and preferably it includes at least two fused ring structures, that is two ring structures that share two adjacent ring atoms.

In one embodiment of the invention the ligating carbon atom may form part of a non-aromatic ring structure which is fused to an aromatic (including heteroaromatic) ring structure. The non-aromatic ring structure may include only carbon ring atoms and preferably it has only 5 ring atoms. The non-aromatic ring structure may include at least one (preferably two) unsaturated carbon-carbon bonds. The non-aromatic ring structure may include at least one non-hydrogen moiety bound to a carbon atom of the non-aromatic ring structure which non-hydrogen moiety does not form part of the aromatic ring structure. The non-hydrogen moiety may comprise an organic group, preferably an organyl group, preferably it comprises an aromatic or heteroaromatic group and preferably it is phenyl. The aromatic ring structure fused to the non-aromatic ring structure may contain more ring atoms than the non-aromatic ring structure, and preferably if it has 6 ring atoms. The aromatic ring structure may include only carbon ring atoms.

In one embodiment of the invention the cyclic organic ligand may comprise indenylidene or a substituted derivative thereof.

The transition metal may comprise a Group VIII metal, preferably Os or Ru, preferably Ru.

The catalyst may include further ligands as defined below.

The metathesis reaction may comprise cross-metathesis (including self metathesis and ethenolysis), ring-opening polymerisation metathesis, ring-closing metathesis, or acyclic diene metathesis.

According to another aspect of the present invention there is provided a compound of formula 3

wherein
M is a transition metal;
$L^1$ is a neutral electron donor ligand;
$L^2$ is a phosphorus containing ligand in the form of a heterocyclic organic compound with a ligating phosphorus atom which ligates with M, and which ligating phosphorus atom is an atom in the heterocyclic ring structure of the heterocyclic organic compound;
$X^1$ and $X^2$ are independently a ligand; and
Z is a cyclic organic ligand in the form of a cyclic organic compound with a ligating carbon atom in the cyclic ring structure of the cyclic organic compound which ligates with M by means of a double bond.

The transition metal M may be a transition metal as described earlier above, and preferably it is Ru.

Preferably the compound is a catalyst, preferably a metathesis catalyst, and preferably a homogeneous metathesis catalyst.

Ligand $L^1$ $L^1$ may be selected from the group consisting of a phosphine, sulfonated phosphine, phosphite, phosphinite, phosphonite, arsine, stibine, amine, amide, imine, nitrosyl, carbene and pyridine. In a preferred embodiment of the invention $L^1$ may be any neutral phosphine ligand or carbene ligand. Preferably $L^1$ is a phosphine preferably a phosphine of the formula $PR^3R^4R^5$, wherein $R^3$, $R^4$ and $R^5$ are each independently an organic group, preferably an organyl group, preferably aryl, $C_1$-$C_{10}$ alkyl or cycloalkyl. Preferably $L^1$ is selected from the group consisting of —P(cyclohexyl)$_3$; —P(cyclopentyl)$_3$; —P(iso-propyl)$_3$; and —P(phenyl)$_3$. Preferably $L^1$ comprises a phosphorus containing ligand as defined in respect of $L^2$. Accordingly $L^1$ may be the same as $L^2$.

In another embodiment of the invention $L^1$ may be selected from a group of heterocyclic compounds containing substituted or unsubstituted five membered rings which may be saturated or unsaturated and which may include at least two adjacent or non adjacent nitrogen ring atoms. Examples of such ligands are illustrated as formulas 4, 5 and 6:

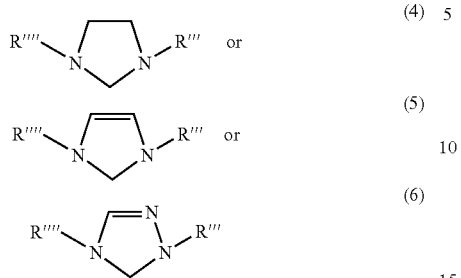

wherein R''' and R'''' may be any group such as H, an organic group (including an organyl group, preferably alkyl, aryl, cycloalkyl, adamantyl or the like, and may be further substituted with functional groups).

Ligand $L^2$ $L^2$ is a phosphorus containing ligand as already defined with reference to formula (3). Preferably, the phosphorus containing ligand comprises a phosphine ligand, preferably a secondary or tertiary phosphine ligand, preferably a tertiary phosphine ligand. The ligating phosphorus atom may also be bound to a further moiety which is not part of the heterocyclic ring structure. The further moiety bound to the ligating phosphorus atom may be an atom, and preferably it is H. In an alternative and preferred embodiment of the invention the said moiety may comprise an organic group, preferably an organyl group. The organyl group may comprise an alkyl, alkenyl, alkynyl, aryl, cycloalkyl, cycloalkenyl, cycloalkyenyl and optionally it may be substituted. Preferably it comprises an alkyl, cycloalkyl or aryl.

Preferably the heterocyclic organic compound has a single heteroatom in the form of the ligating phosphorus atom.

The heterocyclic organic compound may comprise a bicyclic organic compound. Preferably the heterocyclic organic compound includes no unsaturated carbon to carbon bonds. Preferably the two ring structures have at least 3 shared atoms. Preferably the two ring structures do not have more than 12 ring atoms, preferably they have nine ring atoms.

In a preferred embodiment of the invention the phosphine ligand comprises a bicyclic tertiary phosphine having a ligating phosphorus atom which is preferably bound to two first atoms (preferably carbon atoms) in the ring structure with each of said first atoms being bound to two other second atoms (preferably carbon atoms) in the ring structure. Preferably both the second atoms are carbon atoms. It will be appreciated that in this embodiment each first atom is bound to three ring atoms.

In a preferred embodiment of the invention the heterocyclic organic compound comprises a phosphacycloalkane, preferably a phosphabicycloalkane, preferably a phosphabicyclononane, each of which optionally may be substituted. Preferably it comprises a monophosphacycloalkane, preferably a monophosphabicycloalkane, preferably a monophosphabicyclononane. Preferably the compound comprises a tertiary phosphine.

In a preferred embodiment of the invention, the phosphabicyclononane is a 9-phosphabicyclo-[3.3.1]nonane of formula 2a or a 9-phosphabicyclo[4.2.1]nonane of formula 2b or mixtures thereof:

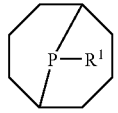

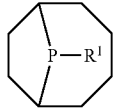

wherein $R^1$ is H, or an organic group (including an organyl group). Preferably $R^1$ is an optionally substituted alkyl, or optionally substituted aryl, or an optionally substituted cycloalkyl.

The phosphabicyclononane may be a compound of formula 2a.

In one embodiment of the invention $R^1$ is alkyl, preferably —$C_{20}H_{41}$ also known as eicosyl. In this instance the ligand is known as eicosyl phoban (that is for both compounds of formula 2a and 2b where $R^1$ is —$C_{20}H_{41}$).

In one preferred embodiment of the invention $R^1$ is cyclohexyl. In this instance the ligand is known as cyclohexyl phoban (that is for both compounds of formula 2a and 2b where $R^1$ is cyclohexyl.

Ligands $X^1$ and $X^2$ $X^1$ and $X^2$ may be independently selected from the group consisting of hydrogen; halide; $C_1$-$C_{20}$ alkyl; aryl; $C_1$-$C_{20}$ alkoxide; aryloxide; $C_3$-$C_{20}$ alkyldiketonate; aryldiketonate; $C_1$-$C_{20}$ carboxylate; arylsulfonate; $C_1$-$C_{20}$ alkylsulfonate; $C_1$-$C_{20}$ alkylthiol; aryl thiol; $C_1$-$C_{20}$ alkylsulfonyl; and $C_1$-$C_{20}$ alkylsulfinyl, the compound being optionally substituted with one or more other moieties selected from the group consisting of $C_1$-$C_{10}$ alkyl; $C_1$-$C_{10}$ alkoxy; aryl and halide. Preferably $X^1$ and $X^2$ are each independently selected from the group consisting of halide; $CF_3CO_2$; $CH_3CO_2$; $CFH_2CO_2$; $(CH_3)_3CO$; $(CF_3)_2(CH_3)CO$; $(CF_3)(CH_3)_2CO$; PhO; MeO; EtO; tosylate; mesylate; and trifluoromethanesulfonate. Preferably $X^1$ and $X^2$ are each independently an anionic ligand, preferably a halide. Preferably $X^1$ and $X^2$ are each chloride.

Ligand Z

Z, the cyclic organic ligand, may be as described above.

In some cases some of the ligands $X^1$, $X^2$, $L^1$, $L^2$ and Z may be linked to each other.

In one preferred embodiment of the invention, the compound of formula 3 may be a compound and of formula 7:

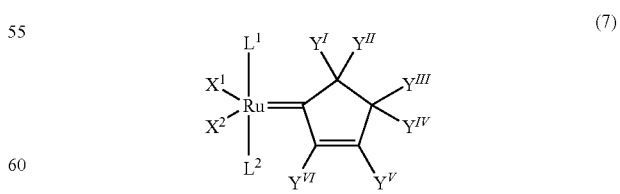

wherein $L^1$, $L^2$, $X^1$ and $X^2$ are as defined above; and each of $Y^I$, $Y^{II}$, $Y^{III}$, $Y^{IV}$, $Y^V$ and $Y^{VI}$ is independently H or a moiety other than H, including an organic group (preferably an organyl group), and at least some of $Y^I$ to $Y^{VI}$ may be linked to each other.

In one preferred embodiment of the invention the compound of formula 7 may be a compound of formula (8)

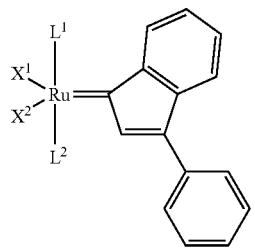

(8)

wherein $X^1$, $X^2$, $L^1$ and $L^2$ are as defined above.

In another preferred embodiment of the invention the compound of formula 7 may be a compound of formula 8a:

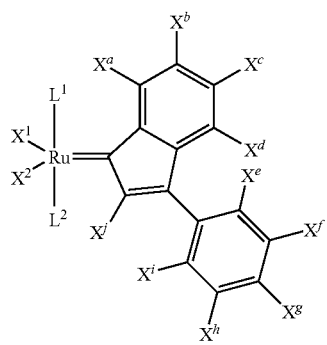

(8a)

wherein $L^1$, $L^2$, $X^1$ and $X^2$ are as defined above; and $X^a$ to $X^j$ are independently hydrogen or a moiety other than H, (preferably halogen, $NO_2$, OR, SR or $NR_2$) provided that at least one of $X^a$ to $X^j$ is not H.

According to another aspect of the invention there is provided the use of a catalyst as described hereinbefore including a catalyst of formula 3, in a metathesis reaction, preferably a homogeneous metathesis reaction.

The reaction is preferably a reaction of at least one olefinic compound in the form of an olefin with one or more double bonds or a compound which includes an olefinic moiety with one or more double bonds. The reaction conditions for the metathesis reaction wherein the catalyst is used may be in accordance to conditions which are well known to a person skilled in the art of metathesis reactions.

Preferably the olefinic compound has a single double bond in the case of a cross-metathesis reaction. Preferably the olefinic compound has two double bonds in the case of a ring-closing metathesis reaction. Preferably the olefinic compound is a cyclic olefin in the case of a ring-opening metathesis polymerisation reaction.

According to a further aspect of the invention there is provided a metathesis product produced by a metathesis reaction using a catalyst substantially as described hereinabove.

The metathesis catalyst may be a catalyst of formula 3 hereinbefore, preferably a homogeneous metathesis catalyst.

According to yet a further aspect of the invention there is provided a catalysed metathesis reaction wherein at least one olefinic compound in the form of an olefin with one or more double bonds or a compound which includes an olefinic moiety with one or more double bonds is subjected to metathesis in the presence of a catalyst of the type described hereinbefore. Preferably the metathesis reaction is a homogeneous metathesis reaction.

According to yet a further aspect of the invention there is provided a process for a ring closing metathesis reaction in the presence of a catalyst of the type described hereinbefore.

According to yet a further aspect of the invention there is provided a process for a ring opening metathesis polymerization reaction in the presence of a catalyst of the type described hereinbefore.

According to yet a further aspect of the invention there is provided a process for a cross or self metathesis reaction in the presence of a catalyst of the type described hereinbefore. The cross metathesis reaction may specifically be an ethenolysis reaction (where one of the two olefinic compounds is ethylene). The metathesis reactions preferably comprise homogeneous metathesis reactions.

The process may include the step of forming the catalyst in situ. The process may then include the steps of adding together of a source of a transition metal; a source of a phosphorus containing ligand in the form of a heterocyclic organic compound with a ligating phosphorous atom suitable for ligating with the transition metal in the source of the transition metal, and which ligating phosphorus atom is an atom in the heterocyclic ring structure of the heterocyclic organic compound; a source of a cyclic organic ligand in the form of a cyclic organic compound with a ligating carbon atom in the cyclic ring structure of the cyclic organic compound which is suitable to ligate with the transition metal in the source of the transition metal by means of a double bond; and at least one olefinic compound to be metathesised which olefinic compound is an olefin or a compound which includes an olefinic moiety.

The source of transition metal may be a source of Ru, and preferably it is an inorganic salt of ruthenium such as $RuCl_3 \cdot xH_2O$.

According to another aspect of the present invention there is provided a method of preparing a compound of formula 3 by reacting a compound of formula 9 with a source of $L^1$ and a source of $L^2$, where $L^1$ and $L^2$ are as defined above:

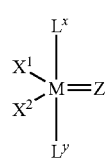

(9)

wherein

M, $X^1$, $X^2$ and Z are as defined with reference to formula 3; and $L^x$ and $L^y$ are the same or different, each is a neutral ligand, and each of $L^x$ and $L^y$ is not the same as $L^1$ or $L^2$.

It will be appreciated that $L^1$ and $L^2$ may be the same and accordingly the source thereof may be the same.

Preferably the compound of formula 9 is a compound of formula 10

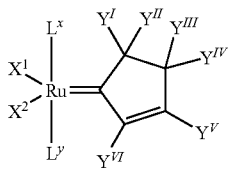

(10)

wherein
$X^1$, $X^2$, $L^x$ and $L^y$ are as defined above; and
each of $Y^I$, $Y^{II}$, $Y^{III}$, $Y^{IV}$, $Y^V$ and $Y^{VI}$ is independently H or a moiety other than H, including an organic group (preferably an organyl group), and at least some of $Y^I$ to $Y^{VI}$ may be linked to each other.

Preferably the compound of formula 10 is a compound of formula 11.

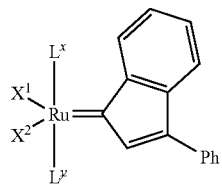

(11)

wherein $X^1$, $X^2$, $L^x$ and $L^y$ are as defined above.

Preferably the compound of formula 10 is a compound of formula 12

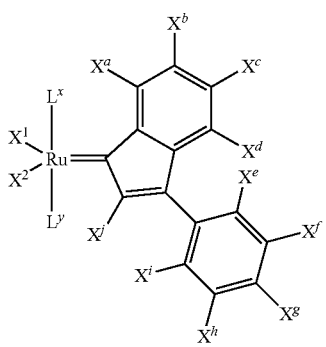

(12)

wherein $X^1$, $X^2$, $L^x$, $L^y$ are as defined above; and $X^a$ to $X^j$ are independently hydrogen or a moiety other than H, (preferably halogen, $NO_2$, OR, SR or $NR_2$) provided that at least one of $X^a$ to $X^j$ is not H.

In a preferred embodiment $L^x$ and $L^y$ are identical and each is triphenylphosphine.

It will be appreciated that the above reaction of preparing a compound of formula 3 is a ligand exchange reaction.

The method of preparation may also include the step of preparing the compounds of formula 9, 10, 11 or 12 and the ligand exchange reaction may be performed in situ after preparation of the compound of formula 9, 10, 11 or 12.

The compound of formula 9 (preferably formulae 10 to 12) may be prepared from reacting a compound consisting of Ru, $X^1$, $X^2$, $L^x$ and $L^y$ only, only with a source of Z. Such a compound consisting of Ru, $X^1$, $X^2$, $L^x$ and $L^y$ only may be a phosphine-ruthenium-halide complex, preferably a phosphine-ruthenium-chloride complex, preferably $(PPh_3)_3 RuCl_2$ or $(PPh_3)_4 Ru Cl_2$. This reaction may be carried out in a polar organic solvent. The resulting compound may be subjected to one or more ligand exchange reactions.

The source of Z may be an alcohol.

The compound consisting of Ru, $X^1$, $X^2$, $L^x$ and $L^y$ only may be prepared by reacting a ruthenium halide (preferably a ruthenium chloride) compound with a source of $L^x$, $L^y$ and also a source of $X^1$ and $X^2$ where $X^1$ and $X^2$ are not halide. Preferably the reaction is between ruthenium chloride and $PPh_3$ only. The reaction may be carried out in a solvent, preferably an organic solvent, preferably a alcohol, preferably ethanol.

A compound of formula 7, preferably of formula 8, may also be prepared by reaction of a ruthenium-di-halide-bis-aryl-dimer complex, preferably [(p-cymene)RuCl$_2$]$_2$, with two ligands chosen from $L^x$, $L^y$, $L^1$ or $L^2$ as defined above, and a di-aryl-propargylic alcohol, preferably 2,2-diphenyl-alkin-1-ol in an organic solvent, preferably followed by exchange of one or two ligands of type $L^x$, $L^y$, $L^1$ or $L^2$ with one or two other ligands of type $L^x$, $L^y$, $L^1$ or $L^2$, followed by isolation of the desired complex through standard procedures.

Without thereby limiting the scope of the invention it will now be further described with reference to the following non-limiting examples.

Example 1

Preparation of Complex (12)

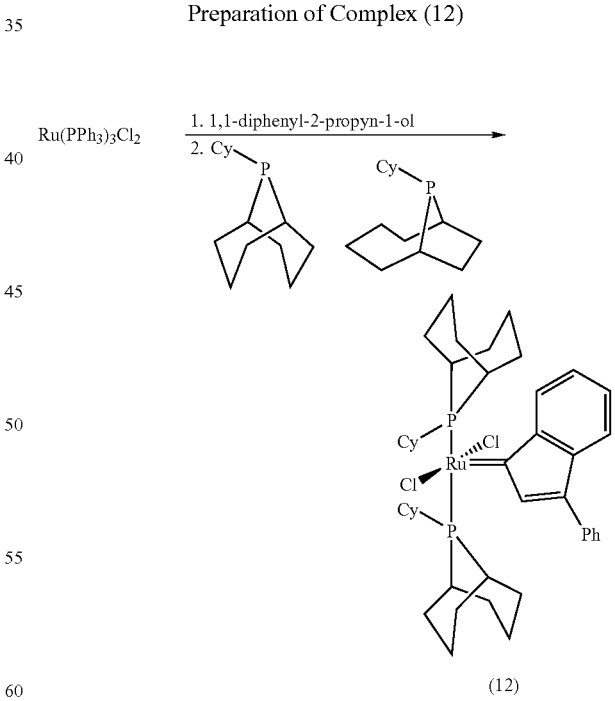

(12)

In a 50 mL round-bottom flask was added Ru(PPh$_3$)$_3$Cl$_2$ (1.0 g, 1.04 mmol) and 1,1-diphenyl-2-propyn-1-ol (330 mg, 1.59 mmol) followed by degassed tetrahydrofuran (80 mL). The mixture was refluxed for 2 h and then the solvent was removed under reduced pressure. Cyclohexylphoban (ca. 3.1 mixture of [3.3.1] and [4.2.1] isomers, 672 mg, 3 mmol) in $CH_2Cl_2$ (20 mL) was added, and the mixture stirred for 24 h. After such time the solvent was removed and the residue taken up in hexane. The solid thus formed was sonicated for 10 minutes and stirred for 1 hour then filtered to give the desired complex (12).

$^{31}P(^1H)$ NMR (121 MHz, $C_6D_6$): δ=22.0 (bs); $^1H$ NMR (300 MHz, $C_6D_6$) δ=8.25 (s, 1H), 7.80-6.75 (m, 9H), 2.80 (s, 4H, PCH of Phoban), 2.26-0.40 (m, 46H, Phoban H).

Single crystals suitable for X-ray diffraction were obtained by recrystallization from evaporation of an ether solution. A crystal structure was obtained (below): $C_{43}H_{60}Cl_2P_2Ru$, $M_r$=810.82, monoclinic, space group P2(1)/c, a=22.336(9), b=17.602(7), c=9.796(4) Å, V=3834(3) Å$^3$, T=173(2) K, Z=4, Á$_{calcd}$=1.357 gcm$^{-3}$, SMART diffractometer, 51939 reflections collected, 6839 unique [$R_{(int)}$=0.1491], $R_1$=0.1137, wR2=0.2231.

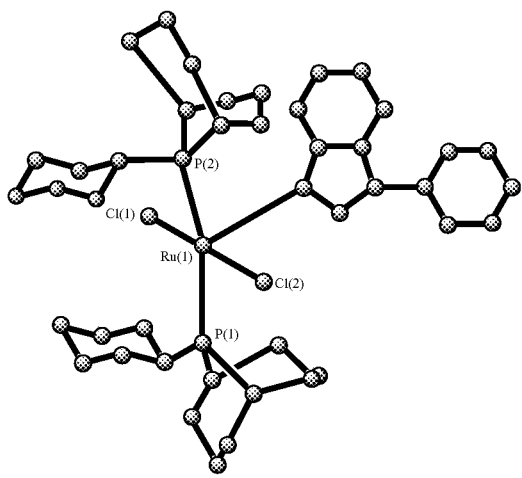

Example 2

Metathesis Using Complex (12) in the Ethenolysis of Methyl Oleate to 1-Decene And 9-Methyldecenoate Methyl oleate (99%) was purchased from Aldrich and passed through a short (2 cm) pad of alumina before use. In a 50 mL stainless-steel autoclave fitted with dip-tube for sampling was charged methyl oleate (12 g, 40.0 mmol). Tetradecane (2.5 g, internal standard) was added and the catalyst (12) of example 1 (0.010 mmol) was weighed and transferred into a Schlenk flask under argon. Toluene (5 mL, degassed) was added to the Schlenk flask and an aliquot (1 mL) of this stock solution was transferred to the autoclave. The autoclave was pressurized (4-20 bar (400 to 2000 kPa) of ethylene) and heated via computerized temperature controller to the desired temperature. Samples were taken at regular intervals using a dip-tube apparatus, and analyzed by GC with an MDN column.

The results are set forth in FIG. 1 which shows the productive turnover obtained using catalyst (12) (S/C=10 000:1) at 10 bar ethylene pressure at various temperatures. TON=Turnover number (number of moles of substrate consumed per mole of catalyst employed. Deg=degrees Celsius.

Example 3

Metathesis Using Complex (12) in the Self-Metathesis of 1-Decene

A 250 mL three-necked round bottom flask was fitted with a reflux condenser, thermometer and septum. A needle was inserted through the septum and connected to a gas supply via a needle valve to ensure a slow and steady stream of argon through the reaction solution. 1-Decene (24 mL, 0.127 mol) was added to the reaction vessel and the reaction was heated to 65° C. The catalyst (12) of example 1 (11.0 mg, 0.014 mmol) was weighed into a custom-made aluminum weighing tray and added to the reaction mixture. Samples were taken at regular intervals via syringe through the septum. Samples were analysed by GC with a Pona column.

Figure 2:
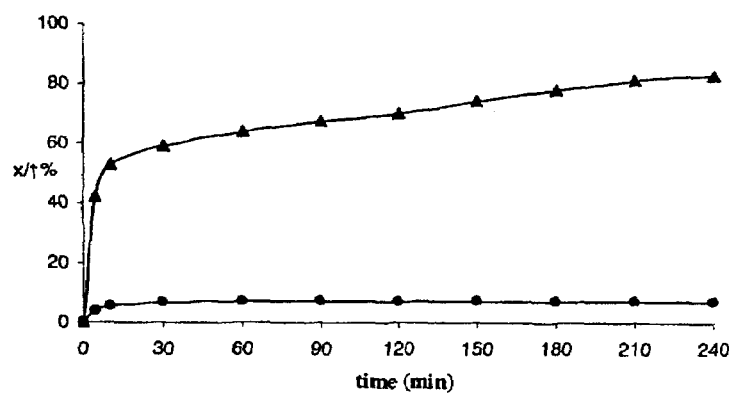
FIG. 2: shows the % conversion obtained using catalyst (12) at 65° C.

The results are set forth in FIG. 2 which shows the % conversion obtained using catalyst (12) at 65 degree C.

It will be appreciated that catalyst (12) was easy to prepare from well accessible, stable and essentially non-toxic starting materials and the catalyst can be isolated and stored. The catalyst exhibited a high catalytic activity, a good compatibility with functional groups and solvents and it need not be activated by any additive.

It will be appreciated that complex a can be used for a variety of metathesis reactions and it will be appreciated that many variations in detail are possible without thereby departing from the spirit and scope of the invention.

The invention claimed is:

1. A transition metal compound including a transition metal, a phosphorus containing ligand, and a cyclic organic ligand; wherein the phosphorus containing ligand is a heterocyclic organic compound with a ligating phosphorus atom which ligates with the transition metal, and which ligating phosphorus atom is an atom in the heterocyclic ring structure of the heterocyclic organic compound; and wherein the cyclic organic ligand is a cyclic organic compound with a ligating carbon atom in the cyclic ring structure of the cyclic organic compound which ligates with the transition metal by means of a double bound.

2. The compound of claim 1 which is a compound of formula (3)

(3)

wherein

M is a transition metal;

$L^1$ is a neutral electron donor ligand;

$L^2$ is a phosphorus containing ligand in the form of a heterocyclic organic compound with a ligating phosphorus atom which ligates with M, and which ligating phosphorus atom is an atom in the heterocyclic ring structure of the heterocyclic organic compound;

$X^1$ and $X^2$ are independently a ligand; and

Z is a cyclic organic ligand in the form of a cyclic organic compound with a ligating carbon atom in the cyclic ring structure of the cyclic organic compound which ligates with M by means of a double bond.

3. The compound of claim 2 wherein M is a Group VIII metal.

4. The compound of claim 3 wherein M is Ru.

5. The compound of claim 2, wherein said compound is a catalyst.

6. The compound of claim 5 which is a metathesis catalyst.

7. The compound of claim 2, wherein $L^1$ is selected from the group consisting of a phosphine, sulfonated phosphine, phosphite, phosphinite, phosphonite, arsine, stibine, amine, amide, imine, nitrosyl, carbene and pyridine.

8. The compound of claim 2, wherein $L^1$ comprises a phosphorus containing ligand in the form of a heterocyclic organic compound with a ligating phosphorus atom which ligates with M, and which ligating phosphorus atom is an atom in the heterocyclic ring structure of the heterocyclic organic compound.

9. The compound of claim 8 wherein $L^1$ and $L^2$ are the same.

10. The compound of claim 2, wherein the heterocyclic organic compound of $L^2$ comprises a bicyclic organic compound.

11. The compound of claim 10 wherein the bicyclic organic compound comprises a phosphabicyclononane.

12. The compound of claim 11 wherein the phosphabicyclononane is a 9-phosphabicyclo-[3.3.1]nonane of formula 2a or a 9-phosphabicyclo[4.2.1]nonane of formula 2b or mixtures thereof:

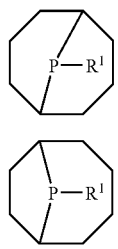

(2a)

(2b)

wherein $R^1$ is H, or an organic group.

13. The compound of claim 12 wherein $R^1$ is an organyl group.

14. The compound of claim 2 wherein $X^1$ and $X^2$ are independently selected from the group consisting of hydrogen; halide; $C_1$-$C_{20}$ alkyl; aryl; $C_1$-$C_{20}$ alkoxide; aryloxide; $C_3$-$C_{20}$ alkyldiketonate; aryldiketonate; $C_1$-$C_{20}$ carboxylate; arylsulfonate; $C_1$-$C_{20}$ alkylsulfonate; $C_1$-$C_{20}$ alkylthiol; aryl thiol; $C_1$-$C_{20}$ alkylsulfonyl; and $C_1$-$C_{20}$ alkylsulfinyl, the compound being optionally substituted with one or more other moieties selected from the group consisting of $C_1$-$C_{10}$ alkyl; $C_1$-$C_{10}$ alkoxy; aryl and halide.

15. The compound of claim 14 wherein $X^1$ and $X^2$ are each independently a halide.

16. The compound of claim 2 wherein the cyclic ring structure of Z including the ligating carbon atom includes at least two fused ring structures that share two adjacent ring atoms.

17. The compound of claim 16 wherein the ligating carbon atom forms part of a non-aromatic ring structure which is fused to an aromatic or heteroaromatic ring structure.

18. The compound of claim 17 wherein the non-aromatic ring structure includes only carbon ring atoms and said ring structure has only 5 ring atoms.

19. The compound of claim 18 wherein the non-aromatic ring structure includes at least one unsaturated carbon-carbon bond.

20. The compound of claim 19 wherein the non-aromatic ring structure includes at least one non-hydrogen moiety bound to a carbon atom of the non-aromatic ring structure, which non-hydrogen moiety does not form part of the aromatic ring structure.

21. The compound of claim 20 wherein the non-hydrogen moiety is an organyl group.

22. The compound of claim 21 wherein the organyl group is phenyl.

23. The compound of claim 17 wherein the aromatic ring structure fused to the non-aromatic ring structure contains more ring atoms than the non-aromatic ring structure.

24. The compound of claim 23 wherein the aromatic ring structure has 6 ring atoms, all being carbon atoms.

25. The compound of claim 2 wherein the compound of formula 3 is a compound of formula 7:

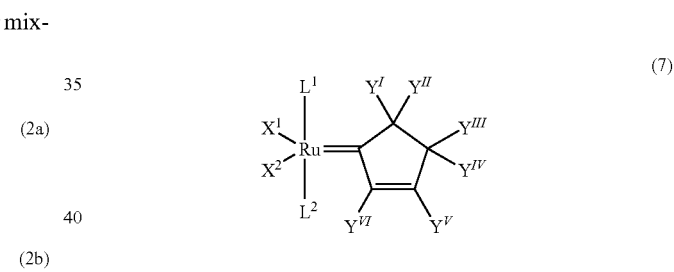

(7)

wherein $L^1$, $L^2$, $X^1$ and $X^2$ are as defined in claim 2; and each of $Y^I$, $Y^{II}$, $Y^{III}$, $Y^{IV}$, $Y^V$ and $Y^{VI}$ is independently H, or a moiety other than H, including an organic group and at least some of $Y^I$ to $Y^{VI}$ may be linked to each other.

26. The compound of claim 25 wherein the compound of formula 7 is a compound of formula 8

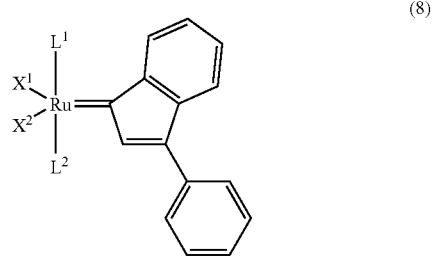

(8)

27. The compound of claim 25 wherein the compound of formula 7 is a compound of formula 8a

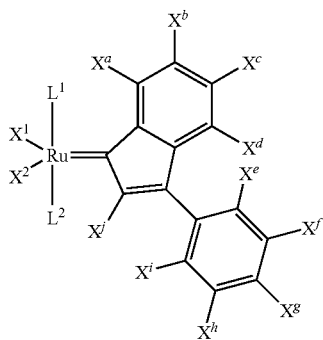

(8a)

wherein
X$^a$ to X$^j$ are independently H or a moiety other than H, provided that at least one of X$^a$ to X$^j$ is not H.

28. A catalysed metathesis reaction wherein at least one olefinic compound in the form of an olefin with one or more double bonds or a compound which includes an olefinic moiety with one or more double bonds is subjected to metathesis in the presence of a catalyst in the form of a compound of claim 1.

29. The reaction of claim 28 which is a homogeneous metathesis reaction.

30. The reaction of claim 28 wherein the catalyst is formed in situ.

31. A method of preparing a compound of formula 3 as set out in claim 2 by reacting a compound of formula 9 with a source of L$^1$ and a source of L$^2$, wherein L$^1$ and L$^2$ is as defined in claim 2

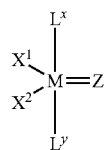

(9)

wherein
M, X$^1$, X$^2$ and Z are as defined with reference to formula 3 in claim 2; and L$^x$ and L$^y$ are the same or different, each being a neutral ligand, and each of L$^x$ and L$^y$ is not the same as L$^1$ or L$^2$.

32. A method of preparing a catalyst in the form of a transition metal compound containing a transition metal in which the method comprises using a phosphorus containing ligand and a cyclic organic ligand as ligands for the catalyst and wherein the phosphorus containing ligand is a heterocyclic organic compound with a ligating phosphorus atom which ligates with the transition metal, and which ligating phosphorus atom is an atom in the heterocyclic ring structure of the heterocyclic organic compound; and wherein the cyclic organic ligand is a cyclic organic compound with a ligating carbon atom in the cyclic ring structure of the cyclic organic compound which ligates with the transition metal by means of a double bond.

33. The method of claim 32 wherein the catalyst is a metathesis catalyst.

34. A method of preparing a transition metal compound catalyst comprising a transition metal in which the method comprises using a phosphorus containing ligand and a cyclic organic ligand as ligands, wherein the phosphorus containing ligand is a heterocyclic organic compound with a ligating phosphorus atom which ligates with the transition metal, and which ligating phosphorus atom is an atom in the heterocyclic ring structure of the heterocyclic organic compound; and wherein the cyclic organic ligand is a cyclic organic compound with a ligating carbon atom in the cyclic ring structure of the cyclic organic compound which ligates with the transition metal by means of a double bond.

35. The method of claim 34 wherein the catalyst is for use in a metathesis reaction.

* * * * *